United States Patent
Jeanjean et al.

(10) Patent No.: US 8,372,440 B2
(45) Date of Patent: Feb. 12, 2013

(54) ANTIFUNGAL FOAM CONTAINING CICLOPIROXOLAMINE AND ZINC PYRITHIONE AND MEDICAL AND COSMETIC APPLICATIONS THEREOF

(75) Inventors: Michel Jeanjean, Castanet Tolosan (FR); Nadine Senegas, Castanet Tolosan (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 469 days.

(21) Appl. No.: 12/596,404

(22) PCT Filed: Apr. 17, 2008

(86) PCT No.: PCT/EP2008/054657
§ 371 (c)(1),
(2), (4) Date: Oct. 16, 2009

(87) PCT Pub. No.: WO2008/135361
PCT Pub. Date: Nov. 13, 2008

(65) Prior Publication Data
US 2010/0129468 A1 May 27, 2010

(30) Foreign Application Priority Data
Apr. 18, 2007 (FR) ...................................... 07 54558

(51) Int. Cl.
*A01N 59/16* (2006.01)
*A61K 33/32* (2006.01)
(52) U.S. Cl. ........ 424/642; 424/702; 424/705; 514/188; 514/254.07; 514/345
(58) Field of Classification Search .................. None
See application file for complete search history.

(56) References Cited

U.S. PATENT DOCUMENTS

| 4,033,895 | A * | 7/1977 | Gerstein ........................ 514/188 |
| 5,650,145 | A | 7/1997 | Saint-Leger |
| 5,798,093 | A | 8/1998 | Farrar et al. |
| 6,211,139 | B1 * | 4/2001 | Keys et al. .................... 510/504 |
| 6,284,234 | B1 | 9/2001 | Niemiec et al. |
| 2004/0241099 | A1 * | 12/2004 | Popp et al. ...................... 424/45 |
| 2005/0170988 | A1 * | 8/2005 | Maillefer et al. ............. 510/407 |
| 2005/0238597 | A1 | 10/2005 | McCook et al. |

FOREIGN PATENT DOCUMENTS

| EP | 0 680 745 A2 | 11/1995 |
| WO | WO-94/16710 A1 | 8/1994 |
| WO | WO 94/16710 A1 * | 8/1994 |
| WO | WO-2005/115336 A2 | 12/2005 |
| WO | WO-2008/076416 A1 | 6/2008 |

OTHER PUBLICATIONS

Roques et al., "In vitro antifungal efficacy of ciclopiroxolamine alone and associated with zinc pyrithione compared to ketoconazole against *Malassezia globosa* and *Malassezia restricta* reference strains" Mycopathologia, 2006, vol. 162, pp. 395-400.*
International Search Report issued Dec. 12, 2008, 3 pages.
French Search Report issued Dec. 7, 2007, 2 pages.
C. Roques et al., "In vitro antifungal efficacy of ciclopiroxolamine alone and associated with zinc pyrithione compared to ketoconazole against *Malassezia globose* and *Malassezia restricta* reference strains", Mycopathologia, 2006, vol. 162, pp. 395-400, XP019452935.

* cited by examiner

*Primary Examiner* — James H. Alstrum-Acevedo
*Assistant Examiner* — Daniel L Branson
(74) *Attorney, Agent, or Firm* — Birch, Stewart, Kolasch & Birch, LLP

(57) ABSTRACT

The invention relates to a composition in the form of an emulsion that can be expanded by an aerosol dispenser, characterized in that it comprises from 15 to 20 volume % of alcohol, from 1 to 10 volume % of $C_3$-$C_8$ polyolen, a thickening agent, at least one non-ionic surfactant, a wetting agent, and one or more active ingredients dissolved or in suspension; the invention also relates to the medical and cosmetic applications thereof.

1 Claim, No Drawings

ANTIFUNGAL FOAM CONTAINING CICLOPIROXOLAMINE AND ZINC PYRITHIONE AND MEDICAL AND COSMETIC APPLICATIONS THEREOF

The invention relates to a product presented in the form of a foam intended for treating seborrheic dermatitis of the scalp and of certain areas of the face.

Seborrheic dermatitis is a frequent but benign dermatosis of adults, and which mainly affects the scalp and the face. Nevertheless it has significant consequences on the life quality of the persons which suffer from it, thus inducing significant therapeutic demand.

Seborrheic dermatitis is of extremely variable intensity, so that the clinical presentation is spread from the simple pellicular condition to more severe forms where the lesions converge into plates which may cover the whole of the scalp.

Itches associated with a sensation of surface burn are the first symptoms thereof.

In the common stage, a so-called dry pellicular condition, the squamae are fine, whitish and not very adherent. They will sprinkle the clothes at the shoulders.

In its typical form, a so-called fatty pellicular condition, the squamae become thicker and larger, often as scabs. Diffuse erythema appears under the squamae, and becomes visible on the outer edges of the lesions, as on the forehead or the temples.

In more severe forms, the lesions may cover the whole of the scalp. At this stage, seborrheic dermatitis becomes very inflammatory with occurrence of prurit, fatty and thick squamae which may emit an unpleasant smell.

Therapy is mainly based on symptomatic treatments of the affected areas.

In the case of seborrhieic dermatitis, itches associated with the pellicular condition of the scalp are most of the time due to massive proliferation of the yeast called Malassezia.

Under normal conditions, Malassezia is found on the skin in 90% of healthy adults and is preferentially localized on the scalp, the external auditory conduits, the face and the middle areas of the back and chest.

Its lipophilicity explains its preferential localization on areas rich in sebaceous glands, and its keratinophilicity explains the absence of lesions at the mucosas.

Malassezia may be responsible for a certain number of pathologies, such as Pityriasis versicolor, pityrosporic folliculitises, neonatal pustulosis . . . .

In the case of seborrheic dermatitis, the action of Malassezia is probably exerted by a pro-inflammatory immunological mechanism.

The essentially local treatment may be based on 2 types of activities which act complementarily on the symptomatology: an anti-inflammatory activity on the one hand and an antifungal activity on the other hand.

Within the scope of the invention, three components have been combined:
1. ciclopiroxolamine, which was used for its rapid action on yeasts of the Malassezia type.
2. zinc pyrithione, which allows inhibition of the proliferation of the yeasts and normalizes the desquamation phenomenon. It also contributes to soothing itches.
3. a wetting agent, the mechanical wetting action of which on the squamae allows them to be rapidly eliminated. It acts by inducing swelling and bursting of cementing substances thereby causing dispersion of the squamae into fine particles.

The benefit of combining ciclopiroxolamine with zinc pyrithione in treating seborrheic dermatitis was clinically demonstrated and has been the subject of publications. Synergy between both of these active ingredients has actually been reported, active dilutions of the combination being twice to eight times greater than that of the active ingredients alone.

The products presently on the market are essentially shampoos, for which the too short contact time with the scalp has a strong adverse effect on their efficiency. Further, the detergent activity specific to the shampoo does not always allow frequent use because of the risk of the sebaceous cycle of being out of control.

To this is added the discomfort experienced by patients affected with seborrheic dermatitis, which need a treatment adapted to the chronicity of the pathology.

The object of the invention is therefore to propose a topical form allowing very frequent use, or even daily use of the latter.

The foam form was retained as being the most suitable for several reasons.

First of all, it allows an increase in the contact time of the active ingredients with the skin, therefore in their penetration into the pilo-sebaceous space.

Unlike shampoos, the removal of which is quasi-immediate by rinsing, the foam has much larger penetration power because of its lipophilic nature therefore of its affinity for the scalp which is also lipophilic. Moreover, because of the evaporation of the alcohol of the propellant, the product is concentrated on the scalp.

Also, because of its expanded form, foam is easy to spread and with it, any local overload on the hair may be avoided, related to overdosage during application.

In order to avoid any risk of unaesthetic burdening of the hair, the base of the foam should prefer volatile compounds. The latter ensure proper dissolution of the active ingredients, facilitating their penetration on the one hand, and they do not leave any undesirable deposit on the hair on the other hand.

The aerosol form allows stabilization of the composition by protecting it against any oxidation.

However, today, there is no base of excipients capable of carrying, in a stable and acceptable way, two antifungal active ingredients such as zinc pyrithione and ciclopiroxolamine.

Because of their physico-chemical characteristics far removed from each other, zinc pyrithione and ciclopiroxolamine actually have different behaviors, causing significant galenic constraints for formulating them in a common base.

Zinc pyrithione appears as a fine particle suspension, the grain size of which is less than 2 microns for more than 95% of them. This fineness allows it to be used in an aerosol formula without risking any blocking of the dispensing channels of the valve or of the diffuser of the aerosol spray. It density much higher than that of water (close to 1.7) makes its suspension in the medium difficult to stabilize.

Ciclopiroxolamine is an organic heterocycle belonging to the family of N-hydroxypyridones. When it is at a concentration of 1%, it requires volume contents in alcohol such as ethanol or isopropanol, close to 35%, combined with a polyol such as hexylene glycol or hexane-1,6-diol, in order to be perfectly solubilized in an emulsified base.

Now, it well-known and technically proven that such a high alcohol content is a destabilizing element for emulsified systems.

Moreover, such amounts of alcohol modify the surface tensions of surfactants, expressed by difficulty in expanding an emulsion as foam via an aerosol, notably a pressurized aerosol with a liquid propellant.

The applicant surprisingly obtained a stable emulsion package in an aerosol can containing a large amount of alcohol, and nevertheless being able to be expanded as a foam, notably in the presence of liquefied gas.

More specifically, the invention relates to a composition as an emulsion which may be expanded as foam by an aerosol dispenser, characterized in that it comprises from 15 to 50% by volume of alcohol, from 1 to 10% by volume of a $C_3$-$C_8$ polyol, a thickener, at least one non-ionic surfactant, a wetting agent and one or more dissolved or suspended active ingredients.

By "foam" is meant a substance formed by confining gas bubbles in a liquid or a solid.

By "aerosol dispenser" is meant any pressurized flask with which a composition may be dispensed as an aerosol or as a foam. As an example, mention will be made of liquefied gas aerosol dispensers, as well as aerosol dispensers with a mechanical pump, currently called "aerosol spray".

By "alcohol" is meant an alkanol comprising 2 to 4 carbon atoms, with a linear or branched chain, such as for example ethanol or isopropanol.

By "thickener" is meant any viscosifying or texturing substance which may be of polymeric nature. Clay will be mentioned as an example.

By "wetting agent" is meant a substance which allows dispersion of particles in a medium. The wetting agent here has the role of dispersing the suspended substance, such as zinc pyrithione.

By "$C_3$-$C_8$ polyol" is meant a compound with a linear, branched or cyclic hydrocarbon chain, comprising 3 to 8 carbon atoms, substituted with at least two hydroxyl groups. As an example, mention will be made of propanediol, hexyleneglycol or hexane-1,6-diol.

By active ingredient is meant any active pharmaceutical or cosmetic substance.

Advantageously, the composition comprises from 20 to 40% by volume of alcohol, more advantageously 35%.

The alcohol is advantageously selected from ethanol and isopropanol.

Advantageously, the composition comprises from 1 to 8% by volume of a $C_3$-$C_8$ polyol, still more advantageously from 1 to 5%.

In order to ensure stabilization of the suspension within the emulsion, it is necessary to resort to polymers of hydrophilic nature capable of forming networks in an aqueous phase and of blocking particle sedimentation phenomena. Indeed, the use of this type of polymer is made indispensable because of the fluidity of the emulsion used in the described invention. They therefore play the role of a thickener.

The thickener may advantageously be selected from polysaccharides of vegetable origin, such as xanthan gum and its derivatives, copolymers of alkyl acrylates and of acrylic and methacrylic acids, notably obtained via a synthesis route, and silicates notably silicates of mineral origin more commonly known as Vecgum® or Bentones®.

The weight proportion of thickener is more advantageously comprised between 0.1 and 1% of the total weight of the composition, more advantageously between 0.2 and 0.7%.

Said at least one non-ionic surfactant may advantageously be selected from waxy or liquid surfactants so as to exclude any risk of chemical interaction with the active ingredients and the emulsion.

The composition may notably comprise a mixture of binary or ternary non-ionic surfactants.

Said at least one non-ionic surfactant may be selected from ethoxylated esters, mixtures of fatty alcohols, ethoxylated $C_{12}$-$C_{18}$ fatty alcohols, hydrogenated and ethoxylated triglycerides, amine alkyl oxides, diethanolamides.

The surfactant weight proportion is advantageously comprised between 1 and 30% of the total weight of the composition, more advantageously between 1 and 15%, more advantageously between 1 and 10%, more advantageously comprised between 2 and 8%, still more advantageously equal to 6%.

The ethoxylated esters may be selected from ethoxylated sorbitan monolaurate (20OE), ethoxylated sorbitan monopalmitate (20OE), ethoxylated sorbitan monostearate (20OE), ethoxylated sorbitan peroleate (40OE) and ethoxylated glyceryl cocoate (7OE). The figure preceding OE designates the number of ethylene oxide units.

The mixtures of fatty acids may be selected from ceteareth-20 (20OE), ceteareth-33 (33OE) and ceteareth-50 (50OE).

Ethoxylated $C_{12}$-$C_{18}$ fatty alcohols may advantageously be selected from laureth-4 (lauric alcohol 4OE) and oleth-10 (oleic alcohol 10OE).

The hydrogenated and ethoxylated triglyceride is advantageously ethoxylated hydrogenated castor oil (40OE), such as for example the product known under the brandname Cremophor RH40 of BASF.

The amine alkoxide is advantageously stearyl dimethylaminoxide, known under the brandname of Amoxyx SO.

The diethanolamide may be selected from isostearamide DEA (isostearamide diethanolamine) and cocamide MEA (cocamide monoethanolamine).

Advantageously, the surfactants may be selected from the following binary or ternary mixtures:
1. Hydrogenated ethoxylated castor oil (40OE)
Sorbitan monostearate (20OE)
2. Ethoxylated oleic alcohol (10OE)
Mixtures of cetyl and stearyl alcohols (50OE)
3. Stearyldimethylaminoxide
Ethoxylated (4OE)
Sorbitan peroleate (40OE)
4. Ceteareth (50OE)
Sorbitan monolaurate (20OE)
Sorbitan peroleate (40OE)
5. Ethoxylated sorbitan monopalmitate (20OE)
Ethoxylated oleic alcohol (10OE)
Ethoxylated coco-triglycerides
6. Ethoxylated oleic alcohol (10OE)
Ethoxylated glyceryl cocoate (7OE)
Ethoxylated hydrogenated castor oil All these surfactants are described in the text book entitled "*International Cosmetic Ingredient Dictionary and Handbook*", 11$^{th}$ edition, 2006.

Advantageously, the composition according to the invention comprises ethoxylated oleic alcohol at a weight concentration comprised between 1 and 10% of the total weight of the composition, ethoxylated glyceryl cocoate at a weight concentration comprised between 1 and 10% of the total weight of the composition, ethoxylated hydrogenated castor oil at a weight concentration comprised between 1 and 10% of the total weight of the composition.

Advantageously, the composition according to the invention comprises ethoxylated oleic alcohol at a weight concentration comprised between 1 and 5% of the total weight of the composition, ethoxylated glyceryl cocoate at a weight concentration comprised between 1 and 5% of the total weight of the composition, ethoxylated hydrogenated castor oil at a weight concentration comprised between 1 and 5% of the total weight of the composition.

The wetting agent is preferably acetamide MEA (acetamide monoethanolamine) or lactamide MEA (lactamide monoethanolamine).

The weight proportion of wetting agent is advantageously comprised between 0.1 and 5% of the total weight of the composition, more advantageously comprised between 1 and 4%, still more advantageously equal to 2%

The weight proportion of each of the active ingredients is advantageously comprised between 0.5 and 2% of the total weight of the composition, preferably equal to 1%.

With the base of excipients of the invention it is possible to formulate systems of particulate suspended active ingredients, such as zinc pyrithione, sulfur, zinc oxide, selenium disulfide and any insoluble active, notably in micronized form.

Moreover, many soluble active ingredients may be formulated by means of the compositions according to the invention. Mention will be made as examples, in addition to ciclopiroxolamine, of imidazolated antifungal compounds such as ketoconazolz, piroctonolamine and magnesium pyridinethione.

The active ingredients present in the composition according to the invention are advantageously ciclopiroxolamine and zinc pyrithione, advantageously in a weight proportion comprised between 0.5 and 2% of the total weight of the composition for each of the active ingredients, preferably equal to 1% for each of the active ingredients.

The composition according to the invention may be packaged as an aerosol dispenser, notably an aerosol dispenser with liquefied gas.

The compositions according to the invention may be advantageously formulated as follows.

| Ingredients | Amounts (g) |
| --- | --- |
| Ciclopiroxolamine | 0.5-2 |
| Zinc pyrithione | 0.5-2 |
| Acetamide MEA | 0.1-5 |
| Cross-linked polymer of acrylates/$C_{10}$-$C_{30}$ alkyl acrylate | 0.1-1 |
| Triethanolamine | 0.1-1 |
| Ethoxylated oleic alcohol | 1-10 |
| Ethoxylated glyceryl cocoate | 1-10 |
| Ethoxylated hydrogenated castor oil | 1-10 |
| Ethanol | 15-40 |
| Hexylene-glycol | 1-10 |
| Demineralized water | qsp 100 |

The liquefied gases are those conventionally used, for example dimethyl ether, hydrofluoroalkanes and binary or ternary mixtures of hydrocarbons selected from butane, propane or isobutene.

The object of the invention also relates to compositions as described earlier, as a drug or as a cosmetic.

The invention will now be illustrated in a non-limiting way by the following example.

A composition according to the invention, containing ciclopiroxolamine and zinc pyrithione was formulated as follows:

| Ingredients | Amounts (g) |
| --- | --- |
| Ciclopiroxolamine | 1 |
| Zinc pyrithione | 1 |
| Acetamide MEA | 2 |
| Cross-linked polymer of acrylates/$C_{10}$-$C_{30}$ alkyl acrylate | 0.6 |
| Triethanolamine | 0.5 |
| Ethoxylated oleic alcohol | 0.5 |
| Ethoxylated glyceryl cocoate | 3 |
| Ethoxylated hydrogenated castor oil | 2.5 |
| Ethanol | 30 |
| Hexylene-glycol | 3 |
| Demineralized water | qsp 100 |

It was then packaged as an aerosol in an amount of 90 g for 10 g of a mixture of butane, propane and isobutane.

The above composition during its use generates abundant foam which is applied and easily spread out on the scalp while causing an immediate soothing effect and is then easily rinsed.

Studies have shown that the above composition allowed clear reduction of the clinical signs associated with seborrheic dermatitis (erythema and prurit) as soon as the first week of treatment.

After 29 days of treatment, more than 65% of the patients were cured from seborrheic dermatitis and more than 34% had their condition clearly improved.

After four weeks of use, the following effects were observed for the quasi-totality of the patients: soothing of the scalp, reduction of red spots, dandruff, squamae and of regreasing of hair.

The invention claimed is:

1. A method for treating seborrheic dermatitis of the scalp and of certain areas of the face, which comprises topical administration of a composition as an emulsion which may be expanded as a foam by an aerosol dispenser, characterized in that said composition has the following centesimal composition:

| Ciclopiroxolamine | 0.5-2 |
| --- | --- |
| Zinc pyrithione | 0.5-2 |
| Acetamide MEA | 0.1-5 |
| Cross-linked polymer of acrylates/$C_{10}$-$C_{30}$ alkyl acrylate | 0.1-1 |
| Triethanolamine | 0.1-1 |
| Ethoxylated oleic alcohol | 1-10 |
| Ethoxylated glyceryl cocoate | 1-10 |
| Ethoxylated hydrogenated castor oil | 1-10 |
| Ethanol | 15-40 |
| Hexylene-glycol | 1-10 |
| Demineralized water | qsp 100. |

* * * * *